United States Patent [19]
Willeke

[11] Patent Number: 5,967,332
[45] Date of Patent: Oct. 19, 1999

[54] METHOD FOR CONCENTRATING AIRBORNE PARTICLES AND MICROORGANISMS BY THEIR INJECTION INTO A SWIRLING AIR FLOW

[75] Inventor: Klaus Willeke, Cincinnati, Ohio

[73] Assignee: SKC, Inc., Eighty Four, Pa.

[21] Appl. No.: 08/889,050

[22] Filed: Jul. 7, 1997

[51] Int. Cl.$^6$ .................................................. B03B 4/00
[52] U.S. Cl. .......................................... 209/132; 209/134
[58] Field of Search .................................. 209/12.1, 131, 209/659, 132, 133, 134, 162, 148, 715, 722, 422, 474, 476

[56] References Cited

U.S. PATENT DOCUMENTS

| | | |
|---|---|---|
| 4,523,682 | 6/1985 | Barmatz et al. ........................ 209/422 |
| 4,894,146 | 1/1990 | Giddings ................................. 209/422 |

*Primary Examiner*—Kenneth Noland
*Attorney, Agent, or Firm*—William L. Krayer

[57] ABSTRACT

A method for concentrating airborne particles and microorganisms by injecting them into a swirling air flow from where they are removed into one or more receiving tubes. The swirling air motion and the aerosol injection into it are achieved by pushing or drawing the airborne particles and microorganisms through one or more nozzles that are directed at an angle towards the surface of the containment vessel. The ratio of air flow rate into the vessel to the air flow rate through the receiving tube is equal to the maximum aerosol concentrating ratio desired.

14 Claims, 3 Drawing Sheets

METHOD FOR CONCENTRATING AIRBORNE PARTICLES AND MICROORGANISMS BY THEIR INJECTION INTO A SWIRLING AIR FLOW

CROSS-REFERENCES TO RELATED APPLICATIONS

Two related co-applications are entitled "SWIRLING AEROSOL COLLECTOR," and "METHOD FOR COLLECTING AIRBORNE PARTICLES AND MICROORGANISMS BY THEIR INJECTION INTO A SWIRLING AIR FLOW."

STATEMENT AS TO THE RIGHTS TO INVENTIONS MADE UNDER FEDERALLY-SPONSORED RESEARCH AND DEVELOPMENT

This invention was not made as part of any federally sponsored research.

BACKGROUND OF THE INVENTION

1. Field of the Invention

The present invention relates to the methods of concentrating the number of airborne particles and microorganisms in the air or gas medium in which they are suspended. In particular, the present invention relates to the method of concentrating aerosol particles by injecting them into a swirling air flow and transferring them to a minor air flow while the major air flow swirls away from the region of particle transfer.

2. Description of the Related Art

Airborne particles and microorganisms are concentrated in air when they are present in such small quantities that they do not yield a sufficiently strong signal when exposed to a given sensing method. For instance, when collected on a filter, there may not be enough particles or microorganisms per unit filter area. Particles or microorganisms suspended in air are herein referred to as "aerosol particles."

The principal method by which airborne particles are concentrated in air is by "virtual impaction." The term "virtual" is used in contrast to "solid-plate." In a "solid-plate impactor," the aerosol flow is directed towards a solid plate so that the high-inertia particles move towards the plate and are removed by it while the low-inertia particles continue with the laterally deflected air flow. In a "virtual impactor," the solid plate is replaced by an air interface (a "virtual" plate) so that the particles are inertially impacted into a dead air volume. Since turbulence in the dead air volume eventually washes the particles back out, unless they have deposited onto the containing wall of the dead volume chamber, some air is usually withdrawn continuously from this air space. The air flow from this receiving volume is typically between $\frac{1}{5}$th to $\frac{1}{20}$th of the total incoming air flow. The remaining air flow is laterally deflected.

This method is also called "dichotomous flow method," because two flows leave the interaction region while only one air flow enters it. The larger particles are transferred to the smaller flow by inertial impaction. The receiving tube usually has an inner diameter that is equal to or slightly larger than the inlet tube, and the tubes are axially aligned with each other. There are usually high particle losses to the inner surfaces for particle sizes at or near the "cut size" of this method. The "cut size" for the particle size distribution is the particle size at which the number of particles in the smaller air flow equals the number of particles in the remaining air flow. The particle losses may be high because particles that do not have enough inertia to be projected into the smaller air flow may have too much inertia to negotiate the sideways deflection with the remaining air flow.

Another method that relates to the present invention is that of aerosol particle removal by centrifugal force. The embodiment of this method is usually referred to as a "cyclone." In a cyclone, the aerosol is drawn into a cylindrical chamber so that the air makes one or more rotations inside before leaving the chamber through a tube at its center. Particles with sufficient inertia move centrifugally toward the inner wall. The problem with this method is that particles that enter the cyclone near its inner effluent tube have a great radial distance to traverse. This method is, therefore, not effective for particles less than a few micrometers in diameter. Also, it does not provide a sharp particle size separation between the collected and uncollected particles. This method does not concentrate aerosol particles in the airborne state but removes them from the air flow.

SUMMARY OF THE INVENTION

The method of the present invention consists of drawing airborne particles or microorganisms into one or more nozzles that are directed at an angle towards the inner surface of a cylindrical vessel or wall. The airborne particles may be solid or liquid, have any shape, and may be biologically or chemically active or inert. This includes particles such as dust, fume, fog, mist, smoke, and smog, and microorganisms such as bacterial cells, fungal spores, pollen grains, viruses, mites, and bacterial fragments. All of the above are herein referred to as aerosol particles. The air flow velocity through the exit plane of the nozzle or nozzles is chosen such that the aerosol particles are thrown at an angle towards the inner surface.

Surrounding the point where the nozzle axis intersects the tangential to the inner wall of the cylindrical container, there is an opening in the wall with a receiving tube attached to it. A fraction of the air flow is extracted by this tube. The axis of this receiving tube is the same as that of the nozzle or it is off-set in the direction of the air flow that is laterally deflected. The turning of the air flow is assisted by the previously deflected air flow that is brought back to the interaction region by its swirling motion in the cylindrical chamber. A fraction of the particles that do not quite reach the receiving tube by inertial forces are moved there by the centrifugal force of the swirling flow. Submicrometer-sized particles may also move across the last short distance by diffusional motion. Thus, the method of this invention differs from the virtual impaction method in that a combination of inertial, centrifugal and diffusional forces move the aerosol particles into the receiving tube or tubes, and the major air flow is laterally deflected in the direction of the swirling air flow by the swirling air flow that intersects the minor, particle-concentrating air flow.

The maximum factor by which the particles in the receiving tube are concentrated equals the ratio of the total air inflow to the air outflow through the receiving tube or receiving tubes. The remaining major air flow exits through a central port. If the cut size for the aerosol particles in the receiving tube or tubes is to be gradual with particle size, the air flow through each nozzle, and the spacing and geometry of each nozzle relative to the receiving tube are chosen so that each nozzle affects a different particle size separation.

Thus, one object of the invention is to concentrate aerosol particles with minimal loss of particles to inner surfaces of the embodiment comprising this method.

Another objective is to have sharp or gradual particle-size separation between the particle fractions in the effluent flow.

Another objective is to have the particle concentrating achieved in a cylindrical arrangement with swirling air flow, in contrast to virtual impaction that is arranged in a single direction.

DESCRIPTION OF THE PREFERRED EMBODIMENTS

Figure 1:
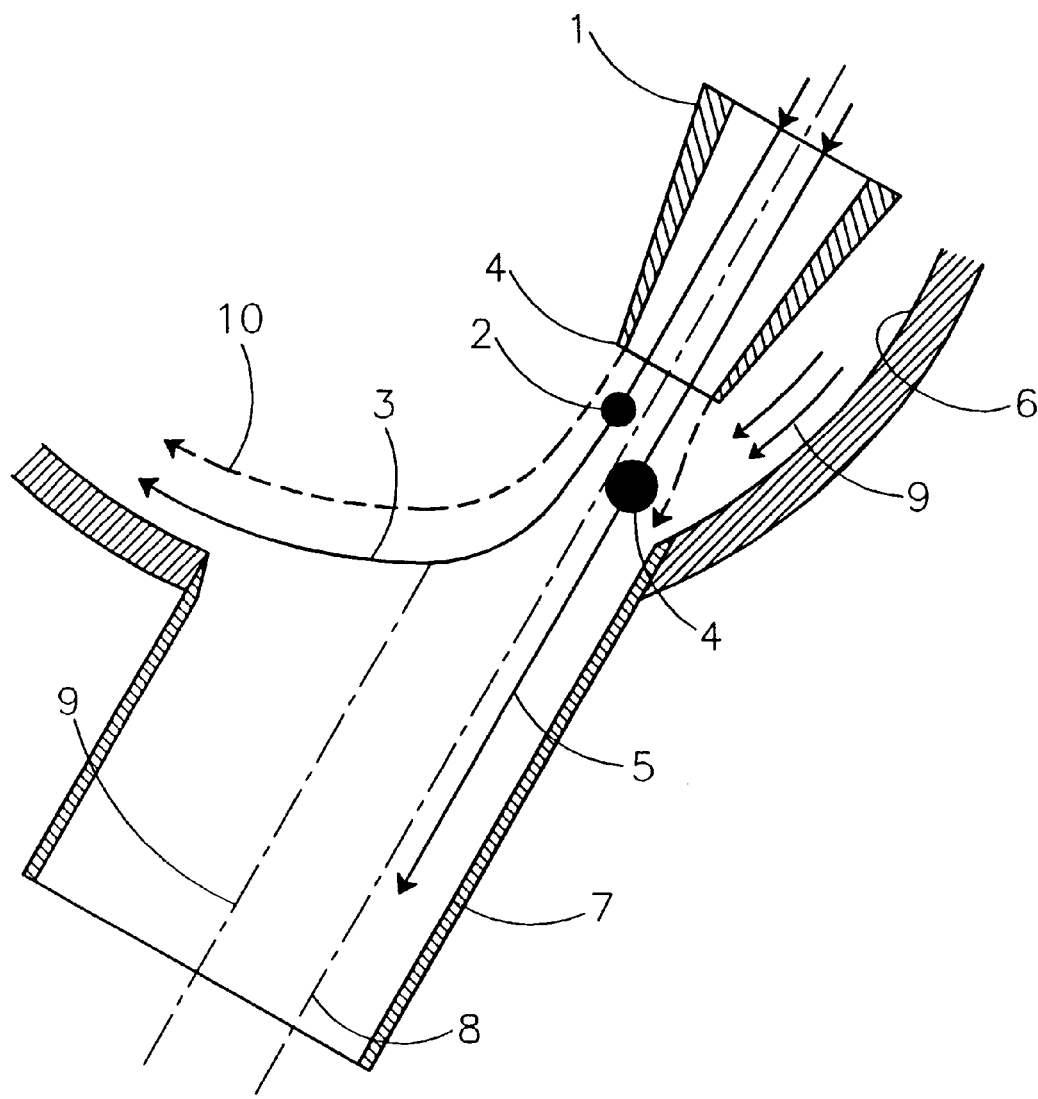
FIG. 1 is a top cross-sectional view illustrating the method of concentrating airborne particles and microorganisms by their injection into a swirling air flow and their removal from there into a receiving tube.

FIG. 1 is a top cross-sectional view that illustrates the method of concentrating airborne particles and microorganisms by their injection into a swirling air flow and their concentrating from there in a receiving tube. Air and airborne particles and microorganisms are drawn into nozzle 1 from where they are ejected towards the swirling air flow 9. The swirling air flow 9 passes along inner vessel surface 6 through the region where air ejected from nozzle 1 interacts with it. The larger particles and microorganisms 4 follow particle trajectories such as 5, indicated by a solid line. The exemplified aerosol particle 4 enters receiving tube 7 from where it is withdrawn at a flow rate that is a fraction of the flow rate through nozzle 1. Smaller aerosol particles 2 follow similar trajectories into receiving tube 7, but may also be turned sideways away from the receiving tube, as indicated by solid line trajectory 3. The majority of air flow from nozzle 1 is redirected along inner surface 6 in the direction of the swirling air flow 9. The majority of the air flow from nozzle 1 and any other nozzles 1 in the circular or near circular path constitutes the swirling air flow 9.

In the preferred embodiment, the nozzle axis 8 is close to the inner wall of receiving tube 7 on the side that is opposite to the swirling air motion. The off-set distance between nozzle axis 8 and receiving tube axis 9 may range from a value near zero and to a value equal to half the inner diameter of receiving tube 7. The inner diameter of receiving tube 7 is equal to or larger than the inner diameter of nozzle 1. The inner diameter of receiving tube 7 can be as much a 50 times larger than the inner diameter of the nozzle exit 4. The off-set between axis 5 and axis 9 creates a distance along the swirling air path over which aerosol particles may pass into the receiving tube by a combination of physical forces comprised of inertial impaction, centrifugation and diffusion. When using this method with microorganisms, autoclavable material such as glass, steel or temperature-resistant plastic is preferable for the inner surfaces of the embodiment, such as nozzle 1 and receiving tube 7.

Figure 2:
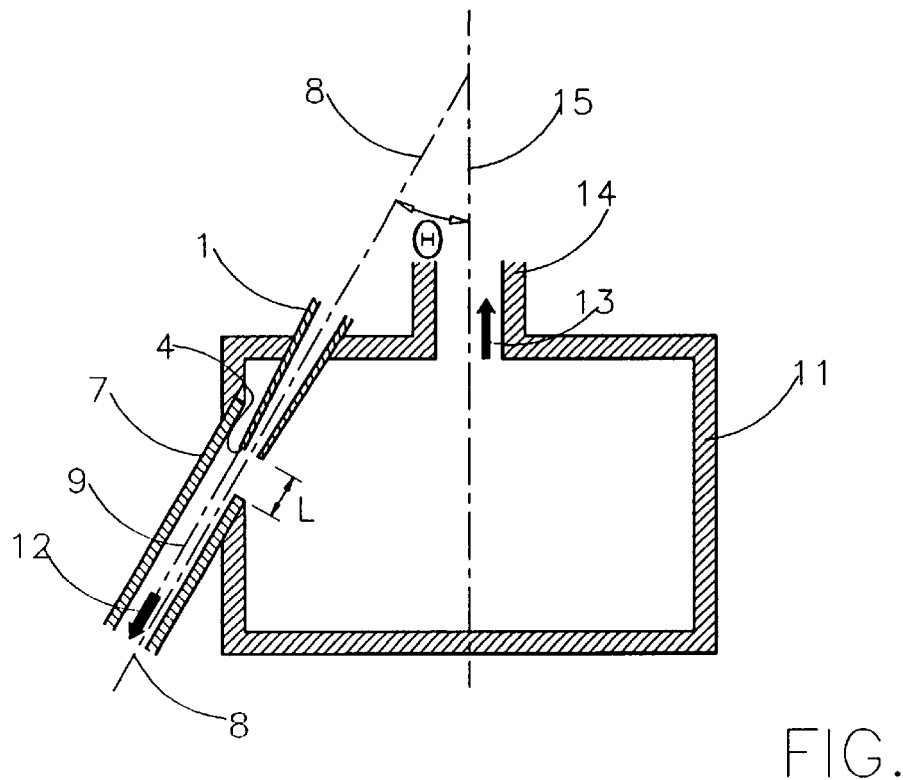
FIG. 2 is a side elevation view with one injection nozzle and one receiving tube shown.
Figure 3:
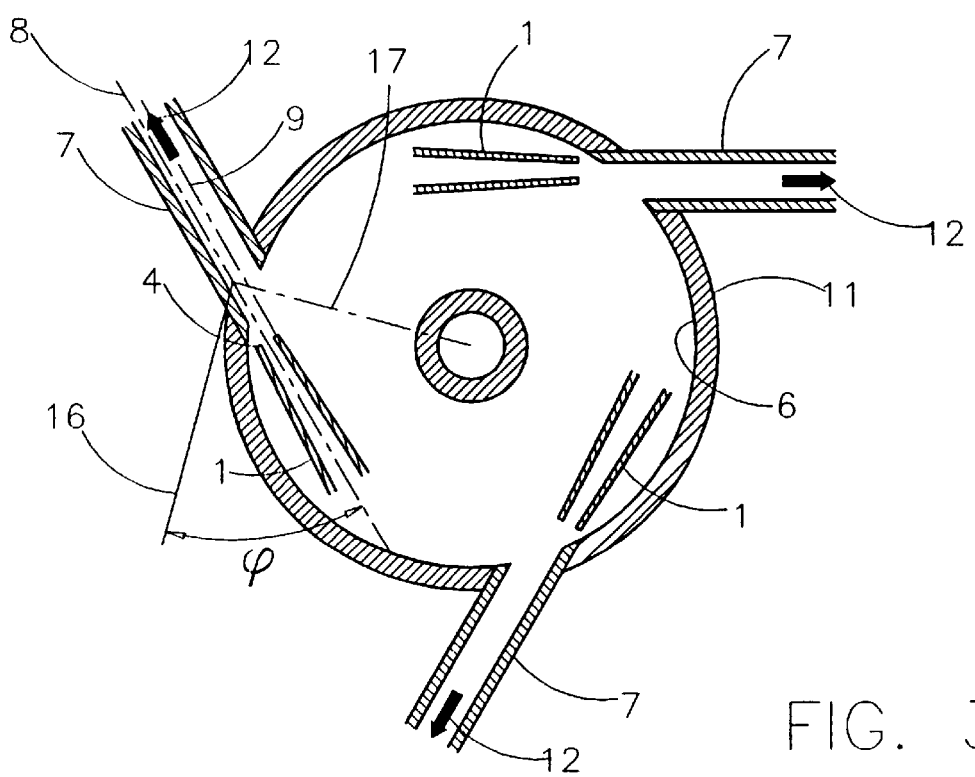
FIG. 3 is a top view showing the placement of three nozzles that inject airborne particles and microorganisms into the swirling air flow and the receiving tubes.

FIG. 2 is a side elevation view with one injection nozzle 1 shown relative to the receiving tube 7. FIG. 3 is a top view showing the placement of three nozzles 1 that inject airborne particles and microorganisms into the swirling air flow and the receiving tubes. One or more nozzles 1 establish the swirling flow along the inner surface 6 of vessel 11. Each nozzle axis 8 is aligned at angle $\phi$ to inner surface tangential 16, and at angle $\theta$ to the vertical 15. Surface tangential 16 is perpendicular to radial line 17. Distance L is along axis line 8 between nozzle exit plane 4 and the furthest point of the inlet to receiving tube 7, measured from where the slanted inlet starts. Distance L is the same for all nozzles 1 when sharp particle size separation is desired between aerosol particles in the concentrated aerosol flow 12 and the major air flow 13 exiting from vessel 11 through exit port 14. Dimension L and the inner exit diameters of nozzles 1 may be different from each other for each nozzle 1, if the particle size separation is to occur over a wide particle size range. The air flow through nozzle exit 4 is at sonic velocity for the concentrating of small particles or microorganisms, and less than sonic for the collection of larger particles 4. Several of these embodiments—each with a different or the same flow rate, and with different or the same body dimensions, such a L, 11, and the number of nozzles 1—may be operated in series or parallel in order to concentrate different particle size fractions.

Angle $\theta$ is typically 60 degrees, but may range from 10 to 90 degrees, and angle $\phi$ is typically 45 degrees, but may range from 10 to 80 degrees. The number of nozzles 1 is one or more. At a typical total incoming flow rate of 12.5 Liter $min^{-1}$, distance L for a three-nozzle embodiment is typically 2 mm, but may range from 0 to 30 mm. Nozzle 1 may also be entirely immersed in receiving tube 7. When three nozzles 1 are used at a flow rate of 12.5 Liter $min^{-1}$, the inner diameter at the nozzle exit plane 4 is typically 0.6 mm or less. All physical dimensions are scalable, depending on the flow rate and the diameter of vessel 11. The method can be used with any curved surface 6.

Experimental Examples

Unless otherwise noted, the experimental examples were performed with the following parameters: total inflow rate= 12.5 Liter $min^{-1}$; minor outflow rate through receiving tubes 7 containing the concentrated aerosol particles=2.5 Liter $min^{-1}$; major outflow rate through exit port 14=12.5 Liter $min^{-1}$; number of nozzles 1=3; $\theta$=60 degrees; $\phi$=45 degrees; exit diameter of each nozzle 1=0.6 mm; inner diameter of vessel 11=32 mm; inner diameter of exit port 14=6 mm. All nozzle axes 8 are offset by about 1.5 mm from receiving tube axis 9 in the manner shown in FIG. 3. The inner diameters of the receiving tubes 7 and distances L are given below. All tests were performed with Polystyrene Latex particles, PSL, suspended in the air drawn into the nozzles 1.

Figure 4:
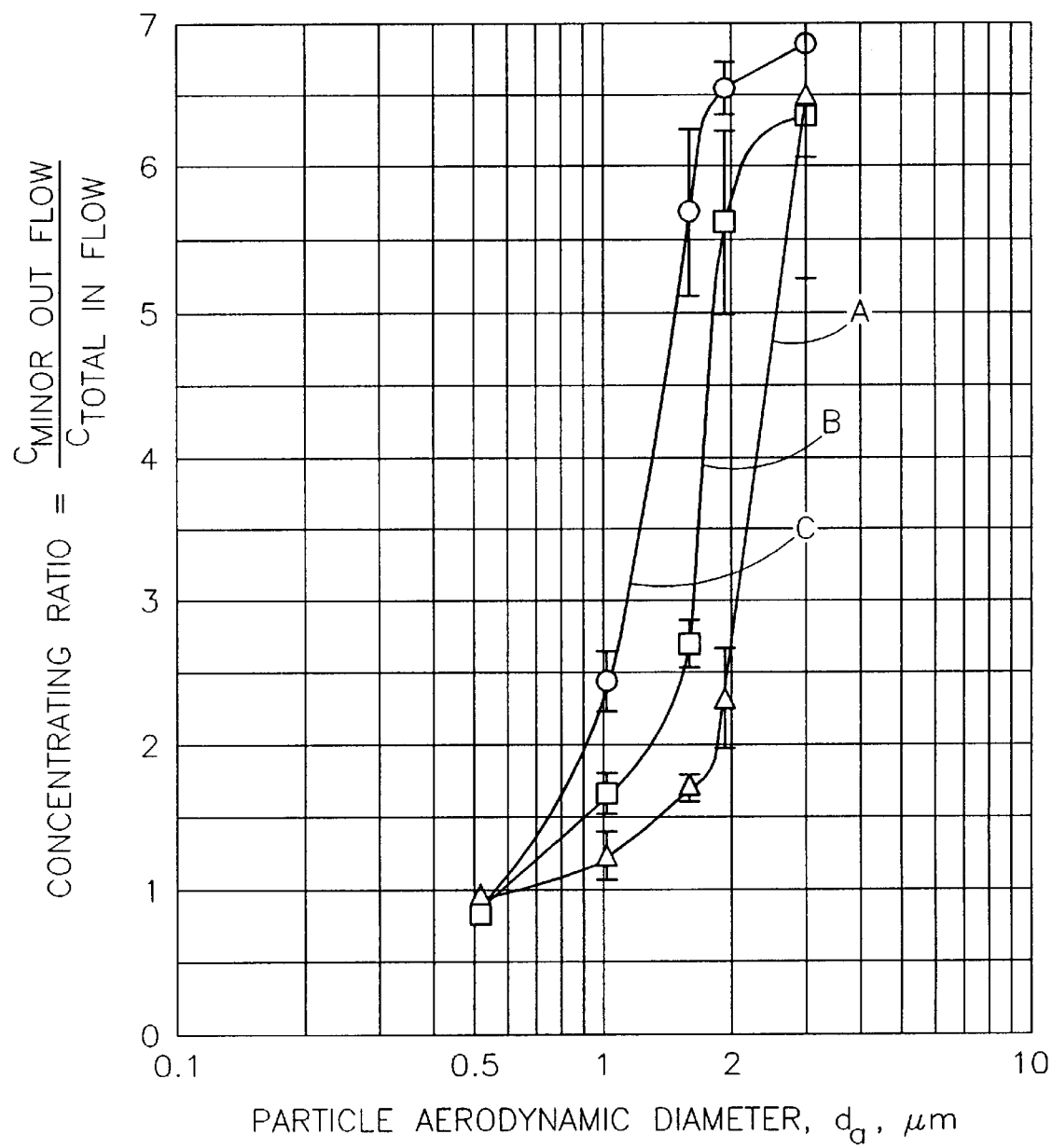
FIG. 4 is a linear-log plot of the method's particle concentrating performance as a function of particle size.

FIG. 4 shows the concentrating ratio as a function of aerodynamic particle diameter for three different receiving tube configurations. The concentrating ratio is defined as the concentration of aerosol particles in the minor air flow through the receiving tubes 7, $C_{MINOR\ OUTFLOW}$, relative to the aerosol particle concentration in the total air inflow to the embodiment, $C_{TOTAL\ INFLOW}$. The particle aerodynamic diameter is indicated as $d_a$ in FIG. 4. Curve A is for a receiving tube with an inner diameter of 4.8 mm (3/16 inch) and L=9 mm; curve B is for a receiving tube with an inner diameter of 4.8 mm (3/16 inch) and L=2 mm; and curve C is for a receiving tube with an inner diameter of 3.2 mm (1/8 inch) and L=2 mm.

Curve A in FIG. 4 is for a condition where the receiving tube diameter is about six times that of the inner nozzle exit diameter, corresponding to a cross-sectional area ratio of 36. For curve A, the nozzle exit plane 4 is placed a considerable distance away from the receiving tube 7. In spite of these adverse conditions, the concentration ratio reaches the maximum possible ratio of about 6 which corresponds to the flow ratio of total inflow to minor outflow. The flows measurements were not sufficiently accurate to result in a concentration ratio exactly equal to 6. Curve B is for the same receiving tube diameter, but with the injection nozzle 1 placed closer into the receiving tube 7. This shifts the size classification to smaller particle sizes. In both cases, the particle size classification is very sharp, as indicated by the steepness of the curve of the concentration ratio with respect to the aerodynamic particle diameter. When distance L is kept the same, but the receiving tube diameter is reduced, curve C, the particle size classification is shifted to an even smaller particle size range.

This experimental example shows that aerosol particle injection into a swirling airflow with particle extraction from that flow by receiving tubes results in the concentrating of the aerosol particle concentration with sharp size classification between the particles leaving through the receiving tubes 7 and those remaining in the airflow and exiting through exit port 14.

While certain preferred embodiments of the present invention have been disclosed in detail, it is to be understood that various modifications in its structure may be adopted without departing from the spirit of the invention or the scope of the following claims.

I claim as my invention:

1. A method for concentrating airborne particles and microorganisms by their injection through one or more nozzles into a swirling air flow in a vessel and removing them from there into one or more receiving tubes, comprising the steps of:
   (1) air and airborne particles and microorganisms, herein referred to as aerosol, being drawn or pushed into one or more nozzles;
   (2) said air and all or a fraction of said particles and said microorganisms flowing through said nozzle or said nozzles, and being ejected from said nozzle or said nozzles at high velocity;
   (3) said ejected air and the said particles and said microorganisms contained in it being directed at an angle towards a curved surface;
   (4) said surface being part of a cylindrical or otherwise shaped vessel that is shaped such that said air and any of said particles and said microorganisms remaining in it are swirled to the region where the same or the next of said nozzles propels said aerosol towards said surface;
   (5) said particles and said microorganisms being removed into said receiving tube or tubes at an air flow rate that is less than the flow rate of air entering the embodiment of this method;
   (6) said receiving tube or said receiving tubes having outlets for removing the aerosol flow rom said receiving tubes;
   (7) said vessel having an outlet port for the remaining air and any remaining fraction of said particles and said microorganisms to leave said vessel;
   (8) said outlets from said receiving tubes being connected to an optional vacuum or suction source; and
   (9) said outlet port from said vessel being connected to an optional vacuum or suction source.

2. The method defined in claim 1, wherein the step of flowing said aerosol through said nozzle or said nozzles comprises nozzle exit holes that are circular or close to circular, each of said exit holes having a diameter between 0.05 mm to 20 mm.

3. The method defined in claim 1, wherein the step of flowing said aerosol through said nozzle or said nozzles comprises one nozzle or several nozzles arranged with approximately equal intervals between the intersections of the nozzle axes and the tangential to the surface of said vessel.

4. The method defined in claim 1, wherein the step of flowing said aerosol through said nozzle or said nozzles comprises an air velocity through said nozzle exit hole where the magnitude of each of said air velocities is between 10 cm sec$^{-1}$ and sonic flow velocity.

5. The method defined in claim 1, wherein the step of directing said ejected air and said particles and said microorganisms at an angle towards said tangential of said curved surface comprises angle θ between 10 and 90 degrees, and angle φ between 10 and 80 degrees, where said angle θ is the angle between the axis of said nozzle and the axis of symmetry of said vessel, and said angle φ is the angle between the axis of said nozzle and the tangential to the said vessel surface where the axis of said nozzle intersects with said vessel surface.

6. The method defined in claim 1, wherein the step of directing said ejected air and said particles and said microorganisms towards said tangential to said curved surface comprises a surface with openings at or near where the axes of said nozzles intersect the tangentials to said inner curved surface.

7. The method defined in claim 1, wherein the step of concentrating said aerosol particles in said receiving tubes comprises said receiving tubes with circular cross-section having an inner diameter between 0.05 mm to 30 mm.

8. The method defined in claim 1, wherein the step of concentrating said aerosol particles in said receiving tubes comprises said receiving tubes with non-circular cross-sections having an inlet cross-sectional area corresponding to those of circular inlets with inner diameter between 0.05 mm to 30 mm.

9. The method defined in claim 1, wherein the step of concentrating said aerosol particles in said receiving tubes comprises said receiving tubes with their axes offset from the nozzle axes by a distance of 0.01 mm to 15 mm.

10. The method defined in claim 1, wherein the step of said aerosol flow through said nozzle or said nozzles comprises between 0.1 and 1000 Liter min$^{-1}$.

11. The method defined in claim 1, wherein the step of said aerosol flow through said nozzle or said nozzles comprises a pressure drop across said nozzle or said nozzles between 0.04 inch (1 mm) and 400 inch (1000 cm).

12. The method defined in claim 1, wherein the step of said aerosol flow through said nozzle or said nozzles comprises particles between 0.001 μm and 500 μm.

13. The method defined in claim 1, wherein the step of said aerosol flow through said receiving tubes comprises between 0.1 and 950 Liter min$^{-1}$.

14. The method defined in claim 1, wherein the step of the air flow consisting of said inflow minus said outflow through the receiving tubes comprises between 0.1 and 990 Liter min$^{-1}$.

* * * * *